(12) United States Patent
Rourk (10) Patent No.: US 11,911,170 B2
(45) Date of Patent: Feb. 27, 2024

(54) DEEP BRAIN SENSING AND STIMULATION PROBE

(71) Applicant: Christopher J. Rourk, Dallas, TX (US)

(72) Inventor: Christopher J. Rourk, Dallas, TX (US)

( * ) Notice: Subject to any disclaimer, the term of this patent is extended or adjusted under 35 U.S.C. 154(b) by 0 days.

(21) Appl. No.: 18/018,404

(22) PCT Filed: Sep. 13, 2022

(86) PCT No.: PCT/US2022/043326
§ 371 (c)(1),
(2) Date: Jan. 27, 2023

(87) PCT Pub. No.: WO2023/039283
PCT Pub. Date: Mar. 16, 2023

(65) Prior Publication Data
US 2023/0263456 A1    Aug. 24, 2023

Related U.S. Application Data (60) Provisional application No. 63/324,271, filed on Mar. 28, 2022, provisional application No. 63/300,097, filed on Jan. 17, 2022, provisional application No. 63/243,510, filed on Sep. 13, 2021.

(51) Int. Cl.
*A61B 5/00*    (2006.01)
*A61B 5/0538*    (2021.01)
*A61B 5/06*    (2006.01)
*A61N 1/05*    (2006.01)

(52) U.S. Cl.
CPC .......... *A61B 5/4064* (2013.01); *A61B 5/0538* (2013.01); *A61B 5/068* (2013.01); *A61B 5/4887* (2013.01); *A61N 1/0534* (2013.01)

(58) Field of Classification Search
CPC ..... A61B 5/4064; A61B 5/0538; A61B 5/068; A61B 5/4887; A61B 5/7221; A61B 2562/0209; A61B 2562/125; A61B 5/055; A61B 5/053; A61B 5/063; A61N 1/0534; A61N 1/3614
See application file for complete search history.

(56) References Cited

U.S. PATENT DOCUMENTS

| 7,957,808 B2 | 6/2011 | Dawant et al. |
| 8,626,298 B2 | 1/2014 | Simon |
| 8,744,564 B2 | 6/2014 | Ward et al. |

(Continued)

FOREIGN PATENT DOCUMENTS

KR    10-2019-009714    8/2019

OTHER PUBLICATIONS

Lempka, et al., "In vivo impedance spectroscopy of deep brain stimulation electrodes", J. Neural Eng., Aug. 2009; 6(4); 20 pages.
(Continued)

*Primary Examiner* — Scott M. Getzow
(74) *Attorney, Agent, or Firm* — Jackson Walker LLP; Christopher J. Rourk (57) ABSTRACT

An electrode for neural sensing and stimulation comprising a first electrode disposed on a probe and a second electrode disposed on the probe, wherein a voltage or impedance is sensed using the first electrode and second electrode.

20 Claims, 6 Drawing Sheets

(56) References Cited

U.S. PATENT DOCUMENTS

| | | | |
|---|---|---|---|
| 8,948,875 B2 | 2/2015 | Paulus et al. | |
| 10,159,839 B2 | 12/2018 | Fried et al. | |
| 11,253,730 B2 | 2/2022 | Zheng et al. | |
| 11,318,311 B2 | 5/2022 | Molnar et al. | |
| 2002/0072686 A1* | 6/2002 | Hoey | A61B 5/4893 600/587 |
| 2009/0024044 A1 | 1/2009 | Virtanen et al. | |
| 2009/0024052 A1* | 1/2009 | Brown | A61B 5/053 600/547 |
| 2009/0093706 A1* | 4/2009 | Zhang | A61B 5/417 382/128 |
| 2011/0022116 A1* | 1/2011 | Lee | A61N 1/36071 607/60 |
| 2011/0060239 A1 | 3/2011 | Gaw | |
| 2011/0080181 A1 | 4/2011 | Sato et al. | |
| 2011/0295350 A1* | 12/2011 | Mercanzini | A61B 5/4094 607/116 |
| 2012/0252685 A1* | 10/2012 | Treynor | G01N 33/6803 435/6.19 |
| 2016/0082263 A1 | 3/2016 | Jaseja | |
| 2018/0333582 A1 | 11/2018 | Grill et al. | |
| 2019/0336748 A1 | 11/2019 | Oxley | |
| 2020/0188675 A1* | 6/2020 | Marceglia | A61N 1/36175 |
| 2021/0085962 A1 | 3/2021 | Patel | |
| 2022/0273184 A1* | 9/2022 | Clark | A61B 5/4082 |

OTHER PUBLICATIONS

Sawan, et al., "Electrode-tissues interface: modeling and experimental validation", Biomed. Mater. 2, (2007), 8 pages.

Salatino, et al., "Glial responses to implanted electrodes in the brain", Nat Biomed Eng., Nov. 2017, 1(11), 37 pages.

Gardner, John, "A history of deep brain stimulation: Technological innovation and the role of clinical assessment tools", Social Studies of Science, 2013, 22 pages.

Notification of Transmittal of The International Search Report and The Written Opinion of the International Searching Authority—The Korean Intellectual Property Office—dated Dec. 27, 2022, for International Application No. PCT/US2022/043326, 10 pages.

* cited by examiner

DEEP BRAIN SENSING AND STIMULATION PROBE

RELATED APPLICATIONS

The present application is a U.S. 371 National Stage application of International Application No. PCT/US22/43326, filed Sep. 13, 2022, which claims benefit of and priority to U.S. Provisional Application No. 63/324,271, filed Mar. 29, 2022, U.S. Provisional Application No. 63/300,097, filed Jan. 17, 2022, and U.S. Provisional Application No. 63/243,510, filed Sep. 13, 2021, each of which is hereby incorporated by reference for all purposes, as if set forth herein in its entirety.

TECHNICAL FIELD

The present disclosure relates generally to neural probes, and more specifically to a deep brain sensing and stimulation probe that allows catecholaminergic neuron electron transport to be detected and used to modify stimulation of neural tissue.

BACKGROUND OF THE INVENTION

Deep brain stimulation is known in the art, and uses an electrode to deliver electrical stimuli to neural tissue. Placement of the probe does not always result in a successful outcome, and requires patient feedback, which is inherently subjective.

SUMMARY OF THE INVENTION

A deep brain sensing and stimulation probe is disclosed and claimed.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE SEVERAL VIEWS OF THE DRAWINGS

Aspects of the disclosure can he better understood with reference to the following drawings. The components in the drawings may be to scale, but emphasis is placed upon clearly illustrating the principles of the present disclosure. Moreover, in the drawings, like reference numerals designate corresponding parts throughout the several views, and in which.

DETAILED DESCRIPTION OF THE INVENTION

In the description that follows, like parts are marked throughout the specification and drawings with the same reference numerals. The drawing figures may be to scale and certain components can be shown in generalized or schematic form and identified by commercial designations in the interest of clarity and conciseness.

Figure 1:
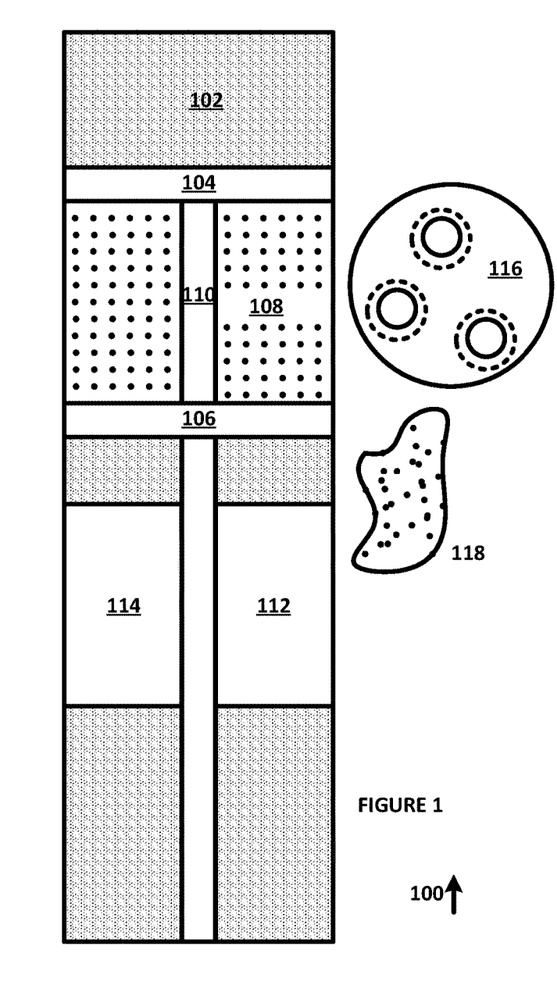
FIG. 1 is a diagram of a deep brain sensing and stimulation probe, in accordance with an example embodiment of the present disclosure.

FIG. 1 is a diagram of a deep brain sensing and stimulation probe 100, in accordance with an example embodiment of the present disclosure. Probe 100 includes body 102, sensing electrodes 104 and 106, quantum dot array 108, lead channel 110 and stimulation electrodes 112 and 114.

Body 102 can be molded, extruded, or otherwise formed of a suitable non-conducting and biocompatible material, such as silicone, polyethylene, polyurethanes, polyureas, polyurethane-ureas or other suitable materials. The lead can have a suitable cross-sectional diameter sufficient to provide mechanical support for the other components of probe 100, but small enough to minimize trauma to the neural tissue that it will be disposed in, such as the range of 0.75 to 1.5 mm, a length of at least 10 cm or longer, as suitable.

Sensing electrodes 104 and 106 can be formed from a suitable conducting metal or material, such as gold, nitinol (nickel titanium alloy) or other suitable alloys. In one example embodiment, sensing electrodes 104 and 106 can be configured to improve the interface to quantum dot array 108, such as by including a surface treatment to improve electron transport between the sensing electrodes 104 and 106 and quantum dot array 108. Although two sensing electrodes 104 and 106 are shown, additional sensing electrodes can also or alternatively be provided. In one example embodiment, additional electrodes can be disposed without being adjacent to quantum dot array 108 or other quantum dot structures, such as to detect catecholaminergic neurons 116 or glial cells 118. As shown by conductive atomic force microscopy (CAFM) tests reported in Rourk, Christopher J., "Indication of quantum mechanical electron transport in human substantia nigra tissue from conductive atomic force microscopy analysis," Biosystems 179 (2019): 30-38, which is hereby incorporated by reference for all purposes as if set forth in its entirety, neuromelanin structures in catecholaminergic neurons like large dopamine neurons of the substantia nigra pars compacta (SNc) are surrounded by layers of ferritin that can conduct electrons by electron tunneling. Glial cells 118 disposed in the SNc between dopamine neuron soma have also been shown to include ferritin layers, which resulted in measured currents in the reported CAFM tests in the areas between SNc dopamine neuron soma, such that sensing electrodes 104 and 106 or other suitable electrodes can detect either catecholaminergic neurons 116 or glial cells 118, with or without quantum dot arrays 108. For example, the impedance measured between electrodes that are spaced apart by a distance greater than the size of glial cell 118 would not be able to readily detect the glial cell 118 but could potentially detect the catecholaminergic neurons 116. The variation in impedance can range in value from greater than $10^{12}$ ohms to values of less than $10^9$ ohms when measured at a point, such as from conductive atomic force microscopy.

In addition, the dopamine metabolism and other homeostatic processes occurring within catecholaminergic neurons 116 can generate triplet electrons that can tunnel through ferritin and neuromelanin organelle structures in those cells, whereas ghat cells 118 do not generate such tunneling currents. As a result, the measured impedance should switch from a large positive impedance to a negative impedance when the electrodes are in contact with the ferritin and neuromelanin organelle structures in those cells, but the measured impedance should only drop from a large resistive value (in tissue with no ferritin or neuromelanin) to a lower resistive value when the electrodes are in contact with ferritin structures in glial cells (reactive impedance can also be measured).

Quantum dot array 108 can be ferritin or other suitable quantum dots that can interface with an electron transport mechanism formed by ferritin in catecholaminergic neurons, which forms layer structures outside of neuromelanin organelles and which is present in glial cells. Electron transport through ferritin in the catecholaminergic neurons facilitates group functioning of those neurons and forms a cellular communications mechanism. The electrons tunnel through the quantum dot array when it is in contact with the ferritin structures, and generate a dynamic voltage that can be sensed using sensing electrodes 104 and 106. Quantum dot array 108 can be encapsulated in a suitable biocompatible encapsulant, such as silicone, polyethylene, polyurethanes, polyureas, polyurethane-ureas, pi-conjugated polymers, polymer nanoparticles or other suitable materials. Quantum dot array 108 will be recognized by a person of skill in the art to include (but not to be limited to) a quantum dot solid, having the physical properties of a quantum dot solid.

Lead channel 110 provides a grounded shield for leads from sensing electrodes 104 and 106 and stimulation electrodes 112 and 114, to prevent high frequency noise from being coupled to the leads. In one example embodiment, shielding can be included around lead channel 110, lead channel 110 can contain separately shielded conductors or other suitable noise suppression techniques can also or alternatively be used, such as differential pairs of conductors for sensing leads.

Stimulation electrodes 112 and 114 can be formed from a suitable conducting metal or material, such as gold, nitinol (nickel titanium alloy) or other suitable alloys, and are configured to be in contact with neural tissue and to provide an electrical stimuli to neural tissue. Stimulation electrodes 112 and 114 are electrically isolated from sensing electrodes 104 and 106, and can include shielding or other suitable electrical isolation mechanisms. Likewise, suitable commercially available deep brain stimulation probes can also or alternatively used, alone, in combination or with suitable modifications to configuration.

In operation, probe 100 is inserted into neural tissue, such as the substantia nigra pars compacta or other suitable tissue. The location of probe 100 relative to the target neurons can be determined using sensing electrodes 104 and 106, which interact with an electron tunneling neural signaling mechanism. When a suitable indexing metric is measured, it can be determined that probe 100 is optimally placed.

Figure 2:
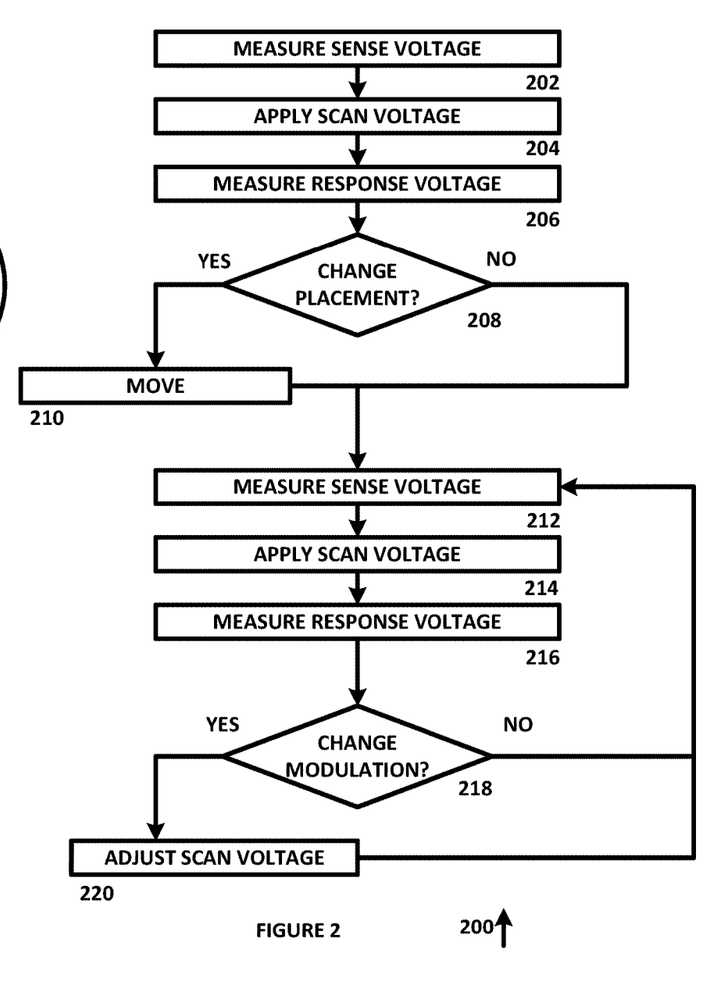
FIG. 2 is a diagram of an algorithm for deploying and using a deep brain sensing and stimulation probe, in accordance with an example embodiment of the present disclosure.

FIG. 2 is a diagram of an algorithm 200 for deploying and using a deep brain sensing and stimulation probe, in accordance with an example embodiment of the present disclosure. Algorithm 200 can be used with probe 100 or other suitable probes, and can be performed by automated sensing and test equipment or other suitable equipment.

Algorithm 200 begins at 202, where a sense voltage is measured. In one example embodiment, the sense voltage can be developed between electrodes, between electrodes that contain a quantum dot array that is configured to interface with ferritin arrays disposed in catecholaminergic neurons, electrodes that encompass other suitable electron tunneling substrates, or other suitable electrodes. The sense voltage can include, direct and alternating frequency components at different frequencies, wave shapes, with modulated signals or other suitable signal components. The algorithm then proceeds to 204.

At 204, a scan voltage is applied. In one example embodiment, the scan voltage can be applied to electrodes that are configured to provide an electrical stimuli to neural tissue, a quantum dot array, other suitable electron tunneling substrates or other suitable neural interface mechanisms. The scan voltage can be a step function voltage at a fixed voltage, a variable voltage, a voltage with different frequency components, a modulated signal or other suitable stimuli. The scan voltage can be applied from stimulating electrodes on the same probe as the sensing electrodes, from stimulating electrodes on a different probe as the sensing electrodes or in other suitable manners. The scan voltage can alternatively be associated with a prosthetic device that is coupled to the probe, such as when a user is learning to control the prosthetic device and one or more feedback signals are generated by the prosthetic device to assist the user, where the scan voltage can be adjusted in response to user observations. The algorithm then proceeds to 206.

At 206, a response voltage is measured. In one example embodiment, the response voltage can be measured at the sense electrodes by measuring the response to the scan voltage with electrodes, with electrodes that detect a signal in the quantum dot array at the same probe, at a different probe, or in other suitable manners. The algorithm then proceeds to 208.

At 208, it is determined whether a placement needs to be changed. In one example embodiment, the placement of an individual probe can be indexed as a function of the sense and scan voltages, to optimally place the probe for sensing and stimulation. In another example embodiment, the placement of one or more additional probes can be modified by incrementing a stepper motor that is coupled to the probe by one or more steps, or other suitable processes can also or alternatively be used. The placement of the electrode can likewise be optimized for a specific response, such as to improve control of a prosthetic device associated with the probe. The algorithm then proceeds to 210.

At 210, the electrode is moved, such as to insert the electrode further into the neural tissue or to remove the electrode to a previous location in the neural tissue. The algorithm then proceeds to 206.

At 212, a sense voltage is measured. In one example embodiment, the sense voltage measurement can be performed on a periodic basis, such as during the normal sensing operation. The algorithm then proceeds to 206.

At 214, a scan voltage is applied. In one example embodiment, the scan voltage can be based on predetermined responses of sense voltages to scan voltages, combinations of scan voltages at different electrodes for specific functional responses or other suitable functions. In another example embodiment, a prosthetic associated with a probe can generate a predetermined scan voltage that can be sensed by the patient to indicate a specific position of a prosthetic, a specific state of the prosthetic or other suitable data. For example, a specific impulse string with a predetermined number of impulses, a specific frequency or other suitable signal processing can be used to provide control. The algorithm then proceeds to 206.

At 216, a response voltage is measured. In one example embodiment, the response voltage can be a function of a state of other neural signals, such as whether a user is awake, whether the user is focusing attention on a prosthetic associated with the probe or other suitable signal information. For example, when a user is focusing attention on a probe, the signals may have a greater amplitude, frequency or other distinguishing characteristics that can be used to detect the state of the user's attention. The algorithm then proceeds to 206.

At 218, it is determined whether a change in modulation is required. In one example embodiment, a plurality of different modulation processes can be used to determine a state of a probe, a state of a user, to cause a change in the state of the user or for other suitable purposes. In this example, different modulations can be used to provide an indication to the user, to allow the user to take certain predetermined actions, for therapeutic purposes or for other suitable purposes. The algorithm then proceeds to 206.

At 220, a scan voltage is adjusted. In one example embodiment, the scan voltage can be changed for a specific purpose, to generate a specific response or for other suitable purposes. The algorithm then proceeds to 206.

In operation, algorithm 200 allows tissues to be analyzed using sense and scan voltages. While algorithm 200 is shown as a flow chart, a person of skill in the art will recognize that it can also or alternatively be implemented as a state diagram, a ladder diagram, using object-oriented programming or in other suitable manners.

Figure 3:
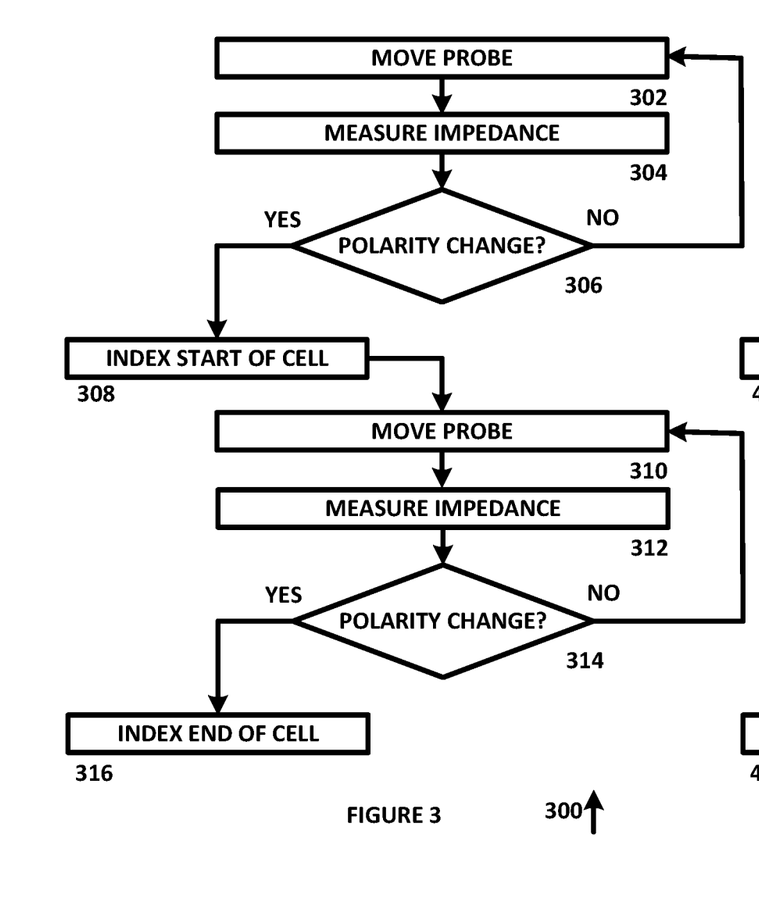
FIG. 3 is a diagram of an algorithm for indexing a deep brain sensing and stimulation probe, in accordance with an example embodiment of the present disclosure.

FIG. 3 is a diagram of an algorithm 300 for indexing a deep brain sensing and stimulation probe, in accordance with an example embodiment of the present disclosure. Algorithm 300 can be used with probe 100 or other suitable probes, and can be performed by automated sensing and test equipment or other suitable equipment.

Algorithm 300 begins at 302, where a probe is moved. In one example embodiment, the probe can be moved using a stepper motor or other suitable devices that can precisely control the placement of the probe to a specific tolerance, such as 10 nanometers or other suitable distances. The algorithm then proceeds to 304.

At 304, an impedance is measured. In one example embodiment, the impedance can be a resistive impedance or a reactance at a specific frequency, a range of frequencies or other suitable impedance measurements. The algorithm then proceeds to 306.

At 306, it is determined whether a polarity change has occurred. In one example embodiment, a polarity change can occur when an impedance changes from a positive impedance to a negative impedance, such as when the tissue structures that the probe is disposed in change from inert to active, such as tissues that conduct tunneling electrons or other suitable active tissues. If it is determined that a polarity change has not occurred, the algorithm returns to 302, otherwise the algorithm proceeds to 308.

At 308, an index is generated to indicate the start of a cell. In one example embodiment, the probe is moved through tissues with positive impedances until it reaches tissues with negative impedances, and indexing is generated to determine a location of the probe within the tissues. The algorithm then proceeds to 310.

At 310, the probe is moved, such as to insert the electrode further into the neural tissue or to remove the electrode to a previous location in the neural tissue. The algorithm then proceeds to 312.

At 312, the impedance is measured. In one example embodiment, the impedance can be a resistive impedance or a reactance at a specific frequency, a range of frequencies or other suitable impedance measurements. The algorithm then proceeds to 314.

At 314, it is determined whether a polarity change has occurred, In one example, embodiment, a polarity change can occur when an impedance changes from a positive impedance to a negative impedance, such as when the tissue structures that the probe is disposed in change from inert to active, such as tissues that conduct tunneling electrons or other suitable active tissues. If it is determined that a polarity change has not occurred, the algorithm returns to 310, otherwise the algorithm proceeds to 316.

At 316, an index is generated to indicate the end of a cell. In one example embodiment, the probe is moved through tissues with negative impedances until it reaches tissues with positive impedances, and indexing is generated to determine a location of the probe within the tissues. In another example embodiment, the indexing process continues as a function of the data that is being measured, such as when a specific profile of tissue responses is known or in other suitable manners.

In operation, algorithm 300 allows tissues with negative impedance characteristics to be identified and an index to be generated, to allow a probe location to be determined. While algorithm 300 is shown as a flow chart, a person of skill in the art will recognize that it can also or alternatively be implemented as a state diagram, a ladder diagram, using object-oriented programming or in other suitable manners.

Figure 4:
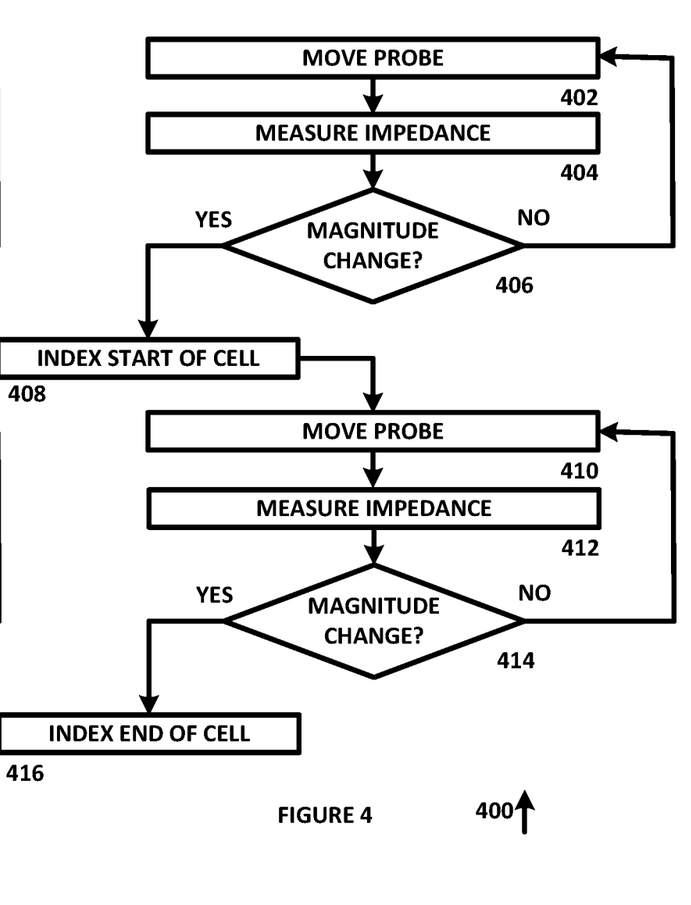
FIG. 4 is a diagram of an algorithm for indexing a deep brain sensing and stimulation probe, in accordance with an example embodiment of the present disclosure.

FIG. 4 is a diagram of an algorithm 400 for indexing a deep brain sensing and stimulation probe, in accordance with an example embodiment of the present disclosure. Algorithm 400 can he used with probe 100 or other suitable probes, and can be performed by automated sensing and test equipment or other suitable equipment.

Algorithm 400 begins at 402, where a probe is moved. In one example embodiment, the probe can be moved using a stepper motor or other suitable devices that can precisely control the placement of the probe to a specific tolerance, such as 10 nanometers or other suitable distances. The algorithm then proceeds to 404.

At 404. an impedance is measured. In one example embodiment, the impedance can be a resistive impedance, a reactance at a specific frequency, a range of frequencies or other suitable impedance measurements. The algorithm then proceeds to 406.

At 406, it is determined whether a magnitude change has occurred. In one example embodiment, a magnitude change can occur when an impedance changes from a higher impedance to a lower impedance, such as when the tissue structures that the probe is disposed change from higher to lower impedance, such as tissues that conduct tunneling electrons or other suitable lower impedance tissues. If it is determined that a magnitude change has not occurred, the algorithm returns to 402, otherwise the algorithm proceeds to 408.

At 408, an index is generated to indicate the start of a cell. In one example embodiment, the probe is moved through tissues with higher impedances until it reaches tissues with lower impedances, and indexing is generated to determine a location of the probe within the tissues. The algorithm then proceeds to 410.

At 410, the probe is moved, such as to insert the electrode further into the neural tissue or to remove the electrode to a previous location in the neural tissue. The algorithm then proceeds to 412.

At 412, the impedance is measured. In one example embodiment, the impedance can be a resistive impedance or a reactance at a specific frequency, a range of frequencies, a combination of impedances or other suitable impedance measurements. The algorithm then proceeds to 414.

At 414, it is determined whether an impedance change has occurred. In one example embodiment, an impedance change can occur when an impedance changes from a lower impedance to a greater impedance, such as when the tissue structures that the probe is disposed change from active to inert, such as tissues that conduct tunneling electrons or other suitable active tissues. If it is determined that a magnitude change has not occurred, the algorithm returns to 410, otherwise the algorithm proceeds to 416.

At 416, an index is generated to indicate the end of a cell. in one example embodiment, the probe is moved through tissues with lower impedances until it reaches tissues with higher impedances, and indexing is generated to determine a location of the probe within the tissues. In another example embodiment, the indexing process continues as a function of the data that is being measured, such as when a specific profile of tissue responses is known or in other suitable manners.

In operation, algorithm 400 allows tissues with varying impedance characteristics to be identified and an index to be generated, to allow a probe location to be determined. While algorithm 400 is shown as a flow chart, a person of skill in the art will recognize that it can also or alternatively be implemented as a state diagram, a ladder diagram, using object-oriented programming or in other suitable manners.

Figure 5:
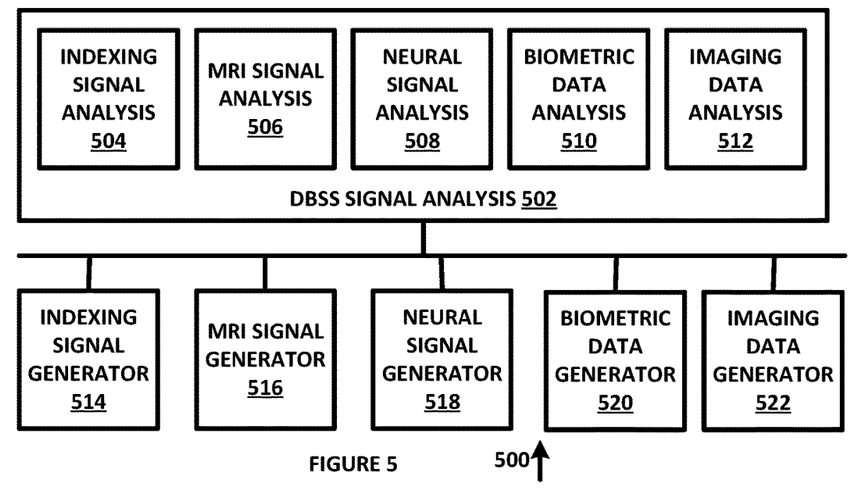
FIG. 5 is a diagram of a system for analyzing deep brain stimulation and sensing signals, in accordance with an example embodiment of the present disclosure.

FIG. 5 is a diagram of a system 500 for analyzing deep brain stimulation and sensing signals, in accordance with an example embodiment of the present disclosure. System 500 includes deep brain stimulation and sensing signal analysis 502, indexing signal analysis 504, magnetic resonance imaging (MRI) signal analysis 506, neural signal analysis 508, biometric data analysis 510, imaging data analysis 512, indexing signal generator 514, MRI signal generator 516, neural signal generator 518, biometric data generator 520 and imaging data generator 522, each of which can be implemented in hardware or a suitable combination of hardware and software.

Deep brain stimulation and sensing signal analysis 502 can be implemented as one or more algorithms stored in a non-transient data memory device associated with a processor that can be loaded into the processor to cause the processor to receive signals from a deep brain stimulation and sensing system and to analyze the signals to identify changes in impedance, absolute values of impedance, changes in voltages, absolute value of voltages and other suitable data, and to perform predetermined analyses of the data. In one example embodiment, deep brain stimulation and sensing signal analysis 502 can receive passive signals that are generated by voltages and currents detected at the leads of a deep brain stimulation and sensing probe, signals that are generated in response to stimulation that is applied to electrodes of a deep brain stimulation and sensing probe and other suitable signals, and can perform signal processing on the data to identify an optimal location for a deep brain stimulation and sensing probe, to generate signals for therapeutic purposes that are delivered by a deep brain stimulation and sensing probe and to perform other suitable functions. In another example embodiment, deep brain stimulation and sensing signal analysis 502 can generate a user interface control that allows an operator to see data that is needed for making a decision on the placement of a deep brain stimulation and sensing probe, such as indexing data from previous patients, data from other signal generators or other suitable data. The user interface control can allow the operator move a deep brain stimulation and sensing probe, such as by one or more stepper motor steps, to stop movement of the deep brain stimulation and sensing probe, to apply predetermined signals to one or more leads of a deep brain stimulation and sensing probe and to perform other suitable functions.

Indexing signal analysis 504 can be implemented as one or more algorithms stored in a non-transient data memory device associated with a processor that can be loaded into the processor to cause the processor to analyze signals from a deep brain stimulation and sensing probe and other suitable sources to identify a location for the deep brain stimulation and sensing probe. In one example embodiment, indexing signal analysis 504 can analyze indexing signal data with data from other patients to identify a confidence score for placement of a deep brain stimulation and sensing probe, can generate patient neural structure profile data for use in generation of a user interface control to allow a user to analyze whether the placement of the current probe was a success and can perform other suitable functions.

MRI signal analysis 506 can be implemented as one or more algorithms stored in a non-transient data memory device associated with a processor that can be loaded into the processor to cause the processor to provide coordinated signals from MRI equipment for use with a deep brain stimulation and sensing probe and other suitable sources to identify a location for the deep brain stimulation and sensing probe. In one example embodiment, MRI signal analysis 506 can analyze MRI data for a patient in coordination with indexing signal data to identify a confidence score for placement of a deep brain stimulation and sensing probe, can generate patient neural structure profile data for use in generation of a user interface control to allow a user to analyze whether the placement of the current probe was a success and can perform other suitable functions.

Neural signal analysis 508 can be implemented as one or more algorithms stored in a non-transient data memory device associated with a processor that can be loaded into the processor to cause the processor to provide coordinated signals from neural signal sensing equipment for use with a deep brain stimulation and sensing probe and other suitable sources to identify a location for the deep brain stimulation and sensing probe. In one example embodiment, neural signal analysis 508 can analyze neural sensing data, such as electroencephalogram data or data from other suitable invasive or non-invasive probes for a patient in coordination with indexing signal data to identify a confidence score for placement of a deep brain stimulation and sensing probe, can generate patient profile data generation of a user interface control to allow a user to analyze whether the placement of the current probe was a success and can perform other suitable functions.

Biometric data analysis 510 can be implemented as one or more algorithms stored in a non-transient data memory device associated with a processor that can be loaded into the processor to cause the processor to provide coordinated signals from biometric data systems for use with a deep brain stimulation and sensing probe and other suitable sources to identify a location for the deep brain stimulation and sensing probe. In one example embodiment, biometric data analysis 510 can analyze biometric data for a patient (such as patient feedback, pulse, respiration, pupil size, galvanic skin response or other suitable biometric data) in coordination with indexing signal data to identify a confidence score for placement of a deep brain stimulation and sensing probe, can generate patient profile data generation of a user interface control to allow a user to analyze whether the placement of the current probe was a success and can perform other suitable functions.

Imaging data analysis 512 can be implemented as one or more algorithms stored in a non-transient data memory device associated with a processor that can be loaded into the processor to cause the processor to provide coordinated signals from imaging equipment for use with a deep brain stimulation and sensing probe and other suitable sources to identify a location for the deep brain stimulation and sensing probe. In one example embodiment, imaging data analysis 512 can analyze imaging data from x-rays, nuclear (ionizing radiation), tomography, echocardiography, magnetic particle imaging, thermal mapping, functional near-infrared spectroscopy imaging, ultrasound, or other suitable imaging data for a patient in coordination with indexing signal data to identify a confidence score for placement of a deep brain stimulation and sensing probe, can generate patient profile data for use in analyzing whether the placement of the current probe was a success and can perform other suitable functions.

Indexing signal generator 514 can he implemented as one or more algorithms stored in a non-transient data memory device associated with a processor that can be loaded into the processor to cause the processor to interface with a deep brain stimulation and sensing probe and to generate and monitor signals from the probe. In one example embodiment, indexing signal generator 514 can switch leads from the probe to a voltage meter, a current meter, a voltage generator, a current generator or other suitable devices, can monitor a first set of leads while applying a signal to a second set of leads and can perform other suitable functions for generating indexing signals associated with the placement of a deep brain stimulation and sensing probe. Indexing signal generator can also generate probe location data, such as by using stepper motor data or other suitable data.

MRI signal generator 516 can be implemented as one or more algorithms stored in a non-transient data memory device associated with a processor that can be loaded into the processor to cause the processor to control a MRI system. In one example embodiment, precise coordination between MRI and deep brain stimulation and sensing probe data can be used to improve the location, indexing and placement of the probe in another example embodiment, the data generated by a MRI device and other devices can also or alternatively be coordinated to improve indexing and placement accuracy for the probe, such as to look for multiple correlations in the data.

Neural signal generator 518 can be implemented as one or more algorithms stored in a non-transient data memory device associated with a processor that can be loaded into the processor to cause the processor to control a neural signal monitoring system. In one example embodiment, precise coordination between neural signals and deep brain stimulation and sensing probe data can be used to improve the location, indexing and placement of the probe. In another example embodiment, the data generated by a neural signal sensing device and other devices can also or alternatively be coordinated with deep brain sensing and stimulation signals to improve indexing and placement accuracy for the probe, such as to look for multiple correlations in the data.

Biometric data generator 520 can be implemented as one or more algorithms stored in a non-transient data memory device associated with a processor that can be loaded into the processor to cause the processor to control a biometric signal monitoring system. In one example embodiment, precise coordination between biometric signals and deep brain stimulation and sensing probe data can be used to improve the location, indexing and placement of the probe In another example embodiment, the data generated by a biometric data. measurement device and other devices can also or alternatively be coordinated with deep brain sensing and stimulation signals to improve indexing and placement accuracy for the probe, such as to look for multiple correlations in the data.

Imaging data generator 522 can be implemented as one or more algorithms stored in a non-transient data memory device associated with a processor that can be loaded into the processor to cause the processor to control an imaging data system. In one example embodiment, precise coordination between imaging data and deep brain stimulation and sensing probe data can be used to improve the location, indexing and placement of the probe In another example embodiment, the data generated by an imaging device and other devices can also or alternatively be coordinated with deep brain sensing and stimulation signals to improve indexing and placement accuracy for the probe, such as to look for multiple correlations in the data.

In operation, system 500 allows a deep brain stimulation and sensing probe to be indexed for precise placement and other suitable purposes, to improve treatment efficacy and reliability. Proper indexing of a deep brain stimulation and sensing probe can help to ensure that the correct neural tissues are being stimulated, can be used to measure signals generated. by electron transport within the tissues and can be used to perform other suitable functions.

Figure 6:
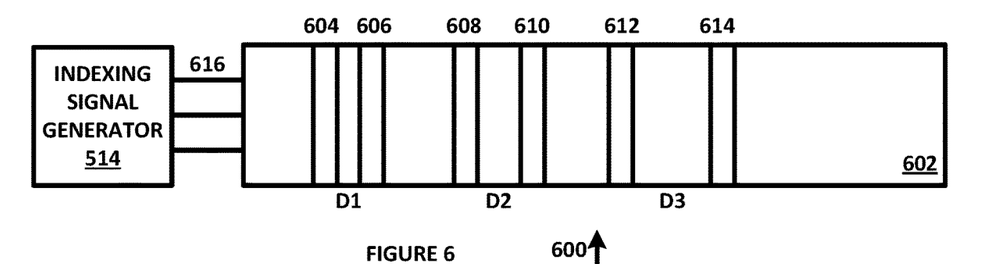
FIG. 6 is a diagram of a probe, in accordance with an example embodiment of the present disclosure.

FIG. 6 is a diagram 600 of a probe 602, in accordance with an example embodiment of the present disclosure. Probe 602 includes electrodes 604 and 606, which are separated by distance D1, electrodes 608 and 610, which are separated by distance D2, and electrodes 612 and 614, which are separated by distance D3. Leads 616 from probe 602 are coupled to indexing signal generator 514 or other suitable systems or components. In one example embodiment, the indexing signal generated by measurements at electrode pairs 604/606, 608/610 and 612/614 can be used to determine the type of tissue or other characteristics of the tissue that the electrode pairs are disposed next to. As discussed, there can be different types of tissue that conduct or generate electrons, such as dopamine neuron soma and glial cells. The different electrode pairs can be used to detect larger structures such as dopamine signal soma, smaller structures such as glial cells, and other structures such as groups of closely coordinated cells. In another example embodiment, different types of signals can be measured by different electrode pairs, as controlled by indexing signal generator 514, such as to measure impedance, voltage, current, or other signals simultaneously, in series or in other suitable manners. Delivery of stimulation can also or alternatively be provided, such as for therapeutic purposes.

Figure 7:
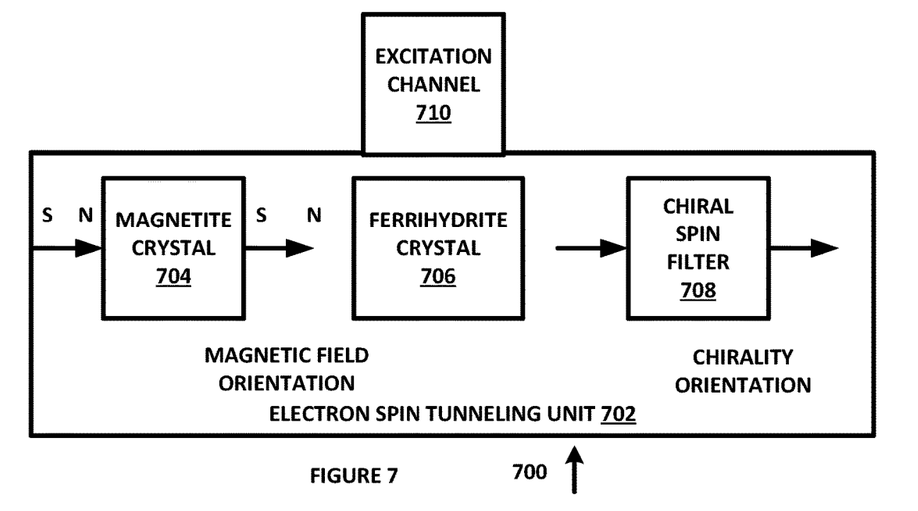
FIG. 7 is a diagram of an electron spin tunneling unit, in accordance with an example embodiment of the present disclosure.

FIG. 7 is a diagram of a system 700 for an electron spin tunneling unit 702, in accordance with an example embodiment of the present disclosure. Electron spin tunneling unit 702 includes magnetite crystal 704, ferrihythite crystal 706, chiral spin filter 708 and excitation channel 710, each of which can be implemented as nanoscale manufactured components on a suitable conducting, semiconducting or non-conducting substrate. Electron spin tunneling unit 702 can be used in quantum dot array 108, to improve coupling between probe 100 or other suitable probes and the surrounding ferritin structures in neural tissues or for other suitable purposes.

Electron spin tunneling unit 702 can be formed as a single unit by suitable nanofabrication processes. In one example embodiment, electron spin tunneling unit can be formed by ion implantation, top-down approaches such as ball milling, laser ablation, electron beam deposition, sputtering, aerosol spray pyrolysis or other suitable top-down approaches, by bottom-up approaches such as co-precipitation, thermal decomposition, sol-gel, micro emulsion, sono-chemical, hydrothermal, microwave assisted, chemical reduction, electrochemical, solvo-thermal, polyol methods, reduction-oxidation hydrothermal processes, or other suitable bottom-up approaches, or in other suitable manners. Some or all components of electron spin tunneling unit 702 can be encapsulated to provide them with corona protection or to protect them from oxidation if necessary, such as by functionalization or surface coating by polymers, metals or organic and/or inorganic stabilizing agents. For example, core-shell and ligand-layer magnetite structures can be used where suitable.

Magnetite crystal 704 can be formed externally and moved to the substrate using a nano-manipulator, can be formed in positon as part of electron spin tunneling unit 702, or can be formed in other suitable manners. Magnetite crystal 704 can be a nanorod synthesized from ferric chloride ($FeCl3$) and diamine hydrate ($H4N2\ H2O$) reagents via a simple, mild reduction-oxidization hydrothermal process in the presence of polyethylene glycol, to provide an easy magnetization axis, or other suitable processes can also or alternatively be used to provide a magnetic field orientation that is aligned with ferrihydrite crystal 706 and a chirality orientation of chiral spin filter 708. In this manner, excitons formed by excitation of electrons in ferrihydrite crystal 706 can be correlated with the chirality orientation of chiral spin filter 708 to facilitate tunneling. While magnetite ($Fe^{2+}$ ($Fe^{3+})_2(O^{2-})_4$) is disclosed, other suitable materials that exhibit orbital electron spin alignment control can also or alternatively be used. Additional information regarding suitable magnetite structures can be found at Wang, Jun, et al. "Growth of magnetite nanorods along its easy-magnetization axis of [1 1 0]." Journal of crystal growth 263.1-4 (2004): 616-619, which is hereby incorporated by reference for all purposes as if set forth herein in its entirety. Magnetite crystal 704 can also or alternatively include one or more magnetization control elements to align the magnetic field orientation along a predetermined axis, so as to align with a chirality orientation of chiral spin filter 708 or other suitable components.

Ferrihydrite crystal 706 can be formed by a suitable top down or bottom up approach and can be pure ferrihydrite or ferrihydrite with suitable ferrihydrite precursors and other elements (such as phosphorus) or compounds (such as water). The structure of the ferrihydrite crystal is optimized to form electron traps to facilitate the generation of excitons that can interact with magnetite crystal 704 and chiral spin filter 708, so as to allow tunneling at high temperatures. While a ferrihydrite (($Fe^{3+})_2O_3 \cdot 0.5H_2O$) crystal is disclosed, other suitable materials can also or alternatively be used that can receive an electron and trap it for a sufficient period of time for the electron to become coherent as a free electron or electron component of an exciton or other quasiparticle.

Chiral spin filter 708 can be formed from a chiral metal-halide perovskite or other suitable materials having a controllable spin selectivity alignment. In one example embodiment, chiral spin filter 708 can be formed from other suitable organic or inorganic materials that can provide chiral induced spin selectivity for an electron, such as a coherent electron generated within ferrihydrite crystal 706 or other suitable electrons. Chiral spin filter 708 can also or alternatively include one or more electric field control elements to align the spin selectivity along a predetermined axis, so as to align with a magnetization axis of magnetite crystal 704 or other suitable components.

Excitation channel 710 can be configured to provide a free electron to ferrihydrite crystal 706 by conduction, tunneling or in other suitable manners. In one example embodiment, excitation channel 710 can provide individual electrons, such as by using a suitable electron emitter having single electron control. Likewise, excitation channel 710 can couple system 100 to an external exciton source, such as a solid state source, a biological source or other suitable sources.

in operation, system 100 allows electron tunneling to be generated and controlled. The temperature at which tunneling occurs and the tunneling distance can he controlled by the size and location of the components of system 100, such as by closely aligning the magnetic field orientation of magnetite crystal 704 and chirality orientation of chiral spin filter 708 and placing these components in close proximity to ferrihydrite crystal 706, or in other suitable manners.

Figure 8:
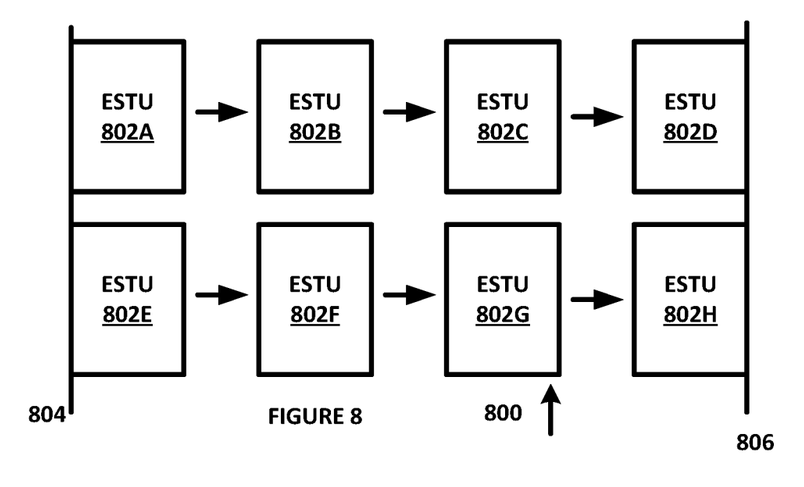
FIG. 8 is a diagram of a system utilizing electron spin tunneling units, in accordance with an example embodiment of the present disclosure.

FIG. 8 is a diagram of a system 800 utilizing electron spin tunneling units 802A through 802H, in accordance with an example embodiment of the present disclosure. Electron spin tunneling units 802A through 802H are disposed along a linear path for electron tunneling between electrodes 804 and 806, as shown by arrows. Because electron spin tunneling units 802A through 802H are directional, they can he aligned to improve the electron tunneling performance. Additional electron tunneling distance can be provided by increasing the relative electrical permittivity of the material disposed between electron spin tunneling units 802A through 802H, and also by operating system 800 at a low energy.

Figure 9:
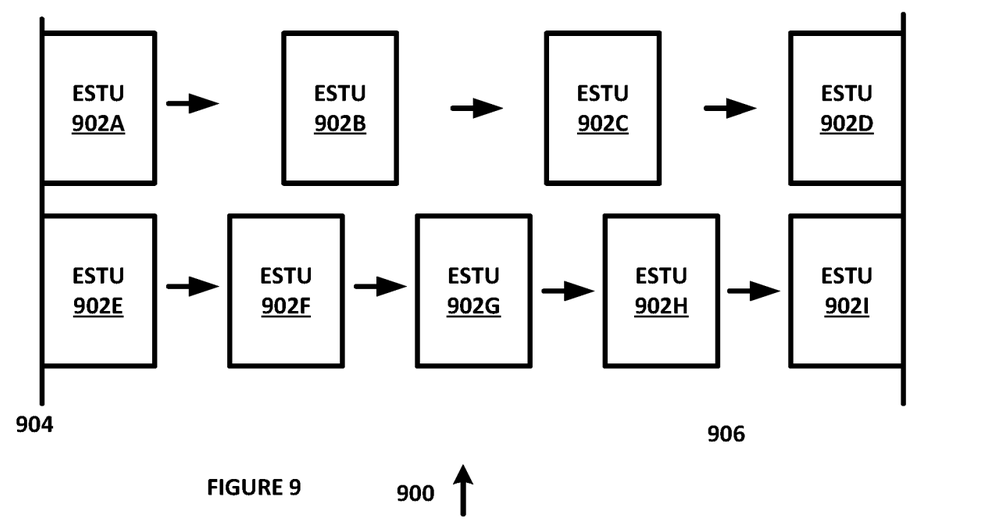
FIG. 9 is a diagram of a second system utilizing electron spin tunneling units, in accordance with an example embodiment of the present disclosure.

FIG. 9 is a diagram of a second system 900 utilizing electron spin tunneling units 902A through 902I, in accordance with an example embodiment of the present disclosure. Electron spin tunneling units 902A through 902I are disposed along parallel electron tunneling axes, as shown by arrows, but have different spacing. As a result, the tunneling response of electron spin tunneling units 902A through 902D of second system 900 to an external electric or magnetic field will be different from the tunneling response of electron spin tunneling units 902E through 902I. In this manner, second system 900 can be used to detect changes in external electric and magnetic fields to a high degree of accuracy.

Figure 10:
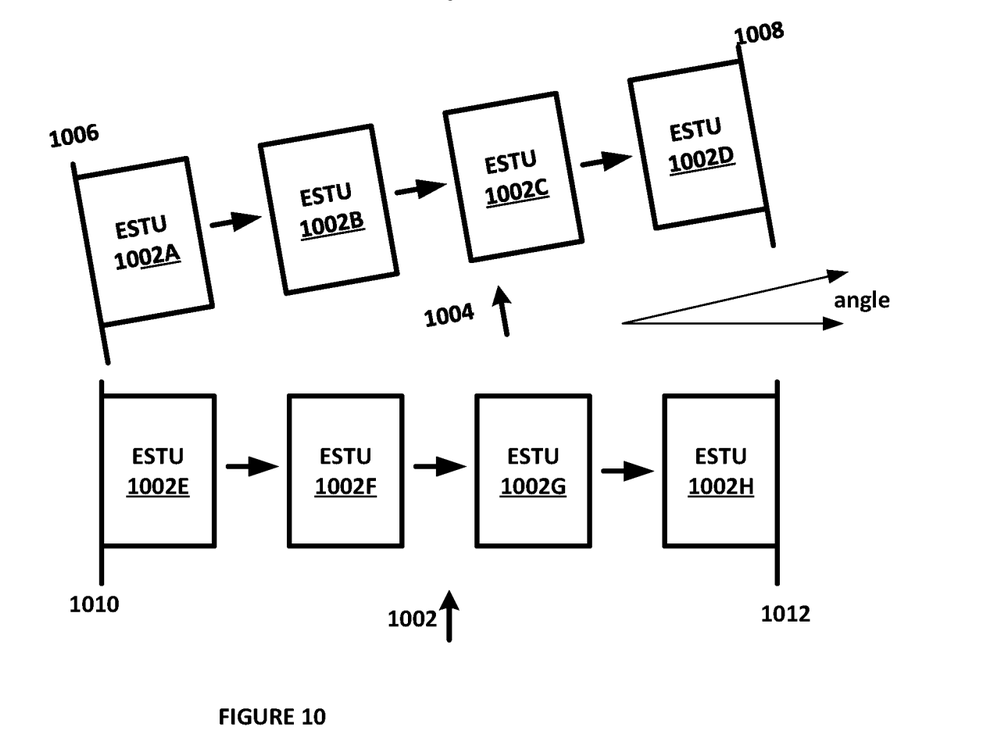
FIG. 10 is a diagram of a third system utilizing electron spin tunneling units, in accordance with an example embodiment of the present disclosure.

FIG. 10 is a diagram of a third system 1000 utilizing electron spin tunneling units 1002A through 1002H, in accordance with an example embodiment of the present disclosure. Electron spin tunneling units 1002A through 1002D are disposed along a different axis than electron spin tunneling units 1002E through 1002H, so as to create an angular displacement between the two axes. In this manner, third system 1000 can be used to detect changes in the orientation of external electric and magnetic fields to a high degree of accuracy.

Figure 11:
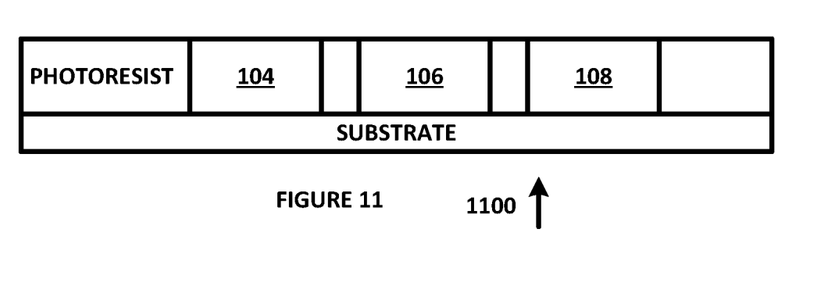
FIG. 11 is a diagram of an electron spin tunneling unit manufacturing process, in accordance with an example embodiment of the present disclosure.

FIG. 5 is a diagram 1100 of an electron spin tunneling unit manufacturing process, in accordance with an example embodiment of the present disclosure. As shown in diagram 1100, a layer of photoresist is formed on a substrate, which can be an insulator, semiconductor or conductor. Wells are formed in the photoresist for one or more of magnetite crystal 1104, ferrihydrite crystal 1106 or chiral spin filter 1108, and the associated element(s) are then formed. In one example embodiment, a ferrihydrite base can be provided by chemical vapor deposition or other suitable processes for both magnetite crystal 1104 and ferrihydrite crystal 1106, and post-processing can be performed on the ferrihydrite base to convert it into magnetite, such as by using an electron source, chemical processes or other suitable processes. The well for chiral spin filter 1108 can then be etched and a suitable material can then be deposited or otherwise formed. Likewise, electrodes and other suitable structures can be provided as discussed and disclosed herein.

Figure 12:
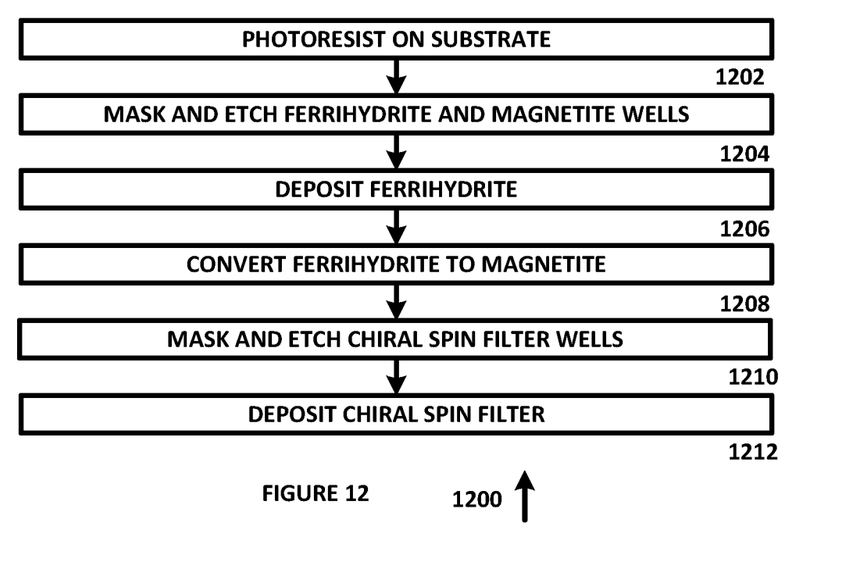
FIG. 12 is an algorithm of the electron spin tunneling unit manufacturing process, in accordance with an example embodiment of the present disclosure.

FIG. 12 is an algorithm 1200 of the electron spin tunneling unit manufacturing process, in accordance with an example embodiment of the present disclosure. Algorithm 1200 begins at 1202, where photoresist is deposited on a substrate. In one example embodiment, the substrate can be an insulator, but a patterned or unpatterned semiconductor substrate, a conducting substrate, a suitable combination of patterned or unpatterned semiconductor substrate and conducting structures in the substrate or other suitable substrates can also or alternatively be used, such as where the electron spin tunneling units are combined with other integrated circuits. The algorithm then proceeds to 1204.

At 1204, the photoresist is masked and ferrihydrite and/or magnetite wells are etched. In one example embodiment, the ferrihydrite and magnetite can be formed from a suitable base material that can then be converted into ferrihydrite or magnetite by a suitable electrical or chemical process, such that the wells for both the ferrihydrite and magnetite are etched at the same time. Alternatively, wells for one of the ferrihydrite or magnetite can be etched first. The algorithm then proceeds to 1206.

At 1206, ferrihydrite is deposited. In one example embodiment, the ferrihydrite and magnetite can be formed and can then be converted into magnetite by a suitable electrical or chemical process. For example, iron Fe3+ oxide can be deposited by chemical vapor deposition and can be converted to magnetite or ferrihydrite, by suitable processes, including additional masking and etching, or other suitable processes can also or alternatively be used. The algorithm then proceeds to 1208.

At 1208, the ferrihydrite, is converted to magnetite. In one example embodiment, the ferrihydrite can be reacted with Fe2+ ions and exposed to a high pH, where magnetite is formed through a multi-step nucleation process mediated by monodisperse FeH—Fe(II) primary particles. The interaction of these primary particles with a transient green rust phase leads to the formation of smaller secondary particles which form the feedstock for magnetite formation. The presence of a polypeptide additive can prevent the formation of green rust as an Fe(II)-rich intermediate phase, and lead to the formation of amorphous aggregates of FeH—Fe(II) particles which subsequently transform into magnetite nanocrystals. Alternatively, the ferrihydrite can be converted to hematite by heating, and then to magnetite by isothermal heating in a flow of a H2—Ar mixture at temperatures between 260 and 360° C. Also or alternatively, Fe2+ or Fe3+ ion implantation, electron implantation or other suitable processes can also or alternatively be used. The algorithm then proceeds to 1210.

At 1210, chiral spin filter wells are formed by masking and etching. In one example embodiment, the chiral spin filters can be disposed in spin axis alignment with a spin axis of the magnetite crystals, to facilitate extended tunneling distances at room temperature. The algorithm hen proceeds to 1212.

At 1212, chiral spin filter structures are formed, such as by deposition or in other suitable manners. In one example embodiment, a chiral metal-halide perovskite layer can be formed in spin filter wells, such as by thermal or laser-induced co-evaporation, sequential thermal evaporation, close space sublimation of organohalides, flash evaporation, ball milling of perovskite precursors for evaporation, sputtering, vapor transport deposition or other suitable processes. The algorithm then ends.

Figure 13:
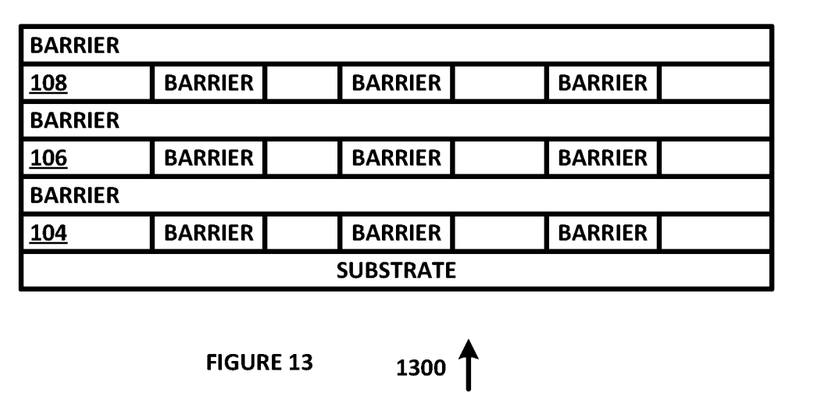
FIG. 13 is a diagram of a second electron spin tunneling unit manufacturing process, in accordance with an example embodiment of the present disclosure.

FIG. 13 is a diagram 1300 of a second electron spin tunneling unit manufacturing process, in accordance with an example embodiment of the present disclosure. As shown in diagram 1300, successive layers of magnetite 1304, ferrihydrite 1306 and chiral spin filter material 1308 are successively formed over a substrate, with a suitable insulating material provided as a barrier. The thickness of the insulating barrier between layers can be adjusted as needed, such as to facilitate manufacturing and prevent conduction of electrons between magnetite 1304, ferrihydrite 1306 and chiral spin filter material 1308 where suitable or if necessary. The device shown in diagram 1300 can generate tunneling electrons extending out from chiral spin filter material 1308 or in other suitable manners.

Figure 14:
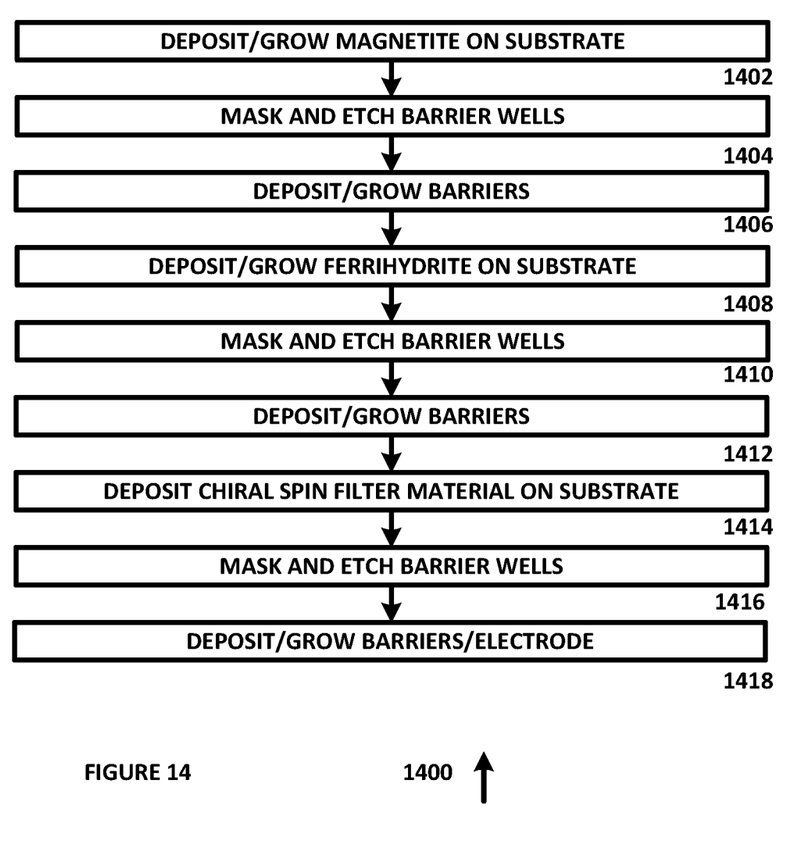
FIG. 14 is an algorithm of the second electron spin tunneling unit manufacturing process, in accordance with an example embodiment of the present disclosure.

FIG. 14 is an algorithm 1400 of the second electron spin tunneling unit manufacturing process, in accordance with an example embodiment of the present disclosure.

Algorithm 1400 begins at 1402, where magnetite is deposited or grown on a substrate.

In one example embodiment, magnetite can be formed by a suitable electrical or chemical process. For example, iron Fe3+ oxide can be deposited by chemical vapor deposition and can be converted to magnetite by suitable processes, including additional masking and etching, or other suitable processes can also or alternatively be used. The algorithm then proceeds to 1404.

At 1404, photoresist is deposited on the magnetite to mask and etch barrier wells. The algorithm then proceeds to 1406.

At 1406, barriers are deposited or grown, The algorithm then proceeds to 1408 where ferrihydrite is deposited or grown. The algorithm then proceeds to 1410, where photoresist is deposited on the ferrihydrite to mask and etch barrier wells. The algorithm then proceeds to 1412.

At 1412, barriers are deposited or grown. The algorithm then proceeds to 1414 where chiral spin filter material is deposited or grown. The algorithm then proceeds to 1416, where photoresist is deposited on the chiral spin filter material to mask and etch barrier wells. The algorithm then proceeds to 1418, where electrodes and/or barriers are deposited or grown. The algorithm then ends.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

As used herein, "hardware" can include a combination of discrete components, an integrated circuit, an application-specific integrated circuit, a field programmable gate array, or other suitable hardware. As used herein, "software" can include one or more objects, agents, threads, lines of code, subroutines, separate software applications, two or more lines of code or other suitable software structures operating in two or more software applications, on one or more processors (where a processor includes one or more microcomputers or other suitable data processing units, memory devices, input-output devices, displays, data input devices such as a keyboard or a mouse, peripherals such as printers and speakers, associated drivers, control cards, power sources, network devices, docking station devices, or other suitable devices operating under control of software systems in conjunction with the processor or other devices), or other suitable software structures. In one exemplary embodiment, software can include one or more lines of code or other suitable software structures operating in a general purpose software application, such as an operating system, and one or more lines of code or other suitable software structures operating in a specific purpose software application. As used herein, the term "couple" and its cognate terms, such as "couples" and "coupled," can include a physical connection (such as a copper conductor), a virtual connection (such as through randomly assigned memory locations of a data memory device), a logical connection (such as through logical gates of a semiconducting device), other suitable connections, or a suitable combination of such connections. The term "data" can refer to a suitable structure for using, conveying or storing data, such as a data field, a data buffer, a data message having the data value and sender/receiver address data, a control message having the data value and one or more operators that cause the receiving system or component to perform a function using the data, or other suitable hardware or software components for the electronic processing of data.

In general, a software system is a system that operates on a processor to perform predetermined functions in response to predetermined data fields. A software system is typically created as an algorithmic source code by a human programmer, and the source code algorithm is then compiled into a machine language algorithm with the source code algorithm functions, and linked to the specific input/output devices, dynamic link libraries and other specific hardware and software components of a processor, which converts the processor from a general purpose processor into a specific purpose processor. This well-known process for implementing an algorithm using a processor should require no explanation for one of even rudimentary skill in the art. For example, a system can be defined by the function it performs and the data fields that it performs the function on. As used herein, a NAME system, where NAME is typically the name of the general function that is performed by the system, refers to a software system that is configured to operate on a processor and to perform the disclosed function on the disclosed data fields. A system can receive one or more data inputs, such as data fields, user-entered data, control data in response to a user prompt or other suitable data, and can determine an action to take based on an algorithm, such as to proceed to a next. algorithmic step if data is received, to repeat a prompt if data is not received, to perform a mathematical operation on two data fields, to sort or display data fields or to perform other suitable well-known algorithmic functions. Unless a specific algorithm is disclosed, then any suitable algorithm that would be known to one of skill in the art for performing the function using the associated data fields is contemplated as falling within the scope of the disclosure. For example, a message system that generates a message that includes a sender address field, a recipient address field and a message field would encompass software operating on a processor that cart obtain the sender address field, recipient address field and message field from a suitable system or device of the processor, such as a buffer device or buffer system, can assemble the sender address field, recipient address field and message field into a suitable electronic message format (such as an electronic mail message, a TCP/IP message or any other suitable message format that has a sender address field, a recipient address field and message field), and can transmit the electronic message using electronic messaging systems and devices of the processor over a communications medium, such as a network. One of ordinary skill in the art would be able to provide the specific coding for a specific application based on the foregoing disclosure, which is intended to set forth exemplary embodiments of the present disclosure, and not to provide a tutorial for someone having less than ordinary skill in the art, such as someone who is unfamiliar with programming or processors in a suitable programming language. A specific algorithm for performing a function can be provided in a flow chart form or in other suitable formats, where the data fields and associated functions can he set forth in an exemplary order of operations, where the order can be rearranged as suitable and is not intended to be limiting unless explicitly stated to be limiting.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

What is claimed is:

1. A system for indexing a neural probe, comprising:
   a probe configured to be inserted into neural tissue;
   an indexing signal generator coupled to the probe and configured to provide a variable frequency signal to the probe; and
   an analysis unit coupled to the probe and configured to process a measured signal to determine an impedance characteristic of surrounding tissue to automatically detect a transition between different types of tissues, wherein the probe comprises a first metal electrode and a second metal electrode and the analysis unit generates an index of locations of the probe in the neural tissue.

2. The system of claim 1 wherein the probe comprises a straight portion containing a plurality of electrodes and the transition is detected between electrodes.

3. The system of claim 1 wherein the probe comprises a straight portion containing a plurality of electrodes and a quantum dot solid.

4. The system of claim 1 wherein the probe comprises a straight portion containing a plurality of electrodes and a plurality of quantum dots.

5. The system of claim 1 wherein the probe comprises a straight portion containing a plurality of electrodes and a plurality of electron spin tunneling units.

6. The system of claim 1 wherein the probe comprises a first metal electrode configured to provide the variable frequency signal to surrounding tissue and a second metal electrode configured to receive the measured signal from the surrounding tissue.

7. The system of claim 1 wherein the probe comprises a plurality of first metal electrodes configured to provide the variable frequency signal to surrounding tissue and a plurality of second metal electrodes configured to receive the measured signal from the surrounding tissue.

8. The system of claim 1 wherein the analysis unit is configured to automatically detect a catecholaminergic neural tissue.

9. A system for indexing a neural probe, comprising:
a probe configured to be inserted into neural tissue;
an indexing signal generator coupled to the probe and configured to provide a variable frequency signal to the probe; and
an analysis unit coupled to the probe and configured to process a measured signal to determine an impedance characteristic of surrounding tissue to automatically detect a transition between different types of tissues wherein the analysis unit is configured to automatically detect a catecholaminergic neural tissue.

10. The system of claim 1 wherein the analysis unit is configured to automatically detect a catecholaminergic neuron.

11. The system of claim 1 wherein the analysis unit is configured to automatically detect a glial cell in catecholaminergic neural tissue.

12. The system of claim 1 wherein the analysis unit is configured to automatically detect a catecholaminergic neural tissue as a function of the impedance characteristic.

13. The system of claim 1 wherein the analysis unit is configured to automatically detect a catecholaminergic neuron as a function of the impedance characteristic.

14. The system of claim 1 wherein the analysis unit is configured to automatically detect a glial cell in catecholaminergic neural tissue as a function of the impedance characteristic.

15. The system of claim 1 wherein the impedance characteristic comprises a change in impedance.

16. The system of claim 1 wherein the impedance characteristic comprises a change in impedance at a frequency.

17. A system for indexing a neural probe, comprising:
a probe configured to be inserted into neural tissue;
an indexing signal generator coupled to the probe and configured to provide a variable frequency signal to the probe; and
an analysis unit coupled to the probe and configured to process a measured signal to determine an impedance characteristic of surrounding tissue to automatically detect a transition between different types of tissues. wherein the impedance characteristic comprises a change in current polarity.

18. The system of claim 1 wherein the analysis unit is configured to analyze MRI data and an index of probe location data to generate modified probe location data.

19. The system of claim 1 wherein the analysis unit is configured to analyze MRI data and an index of probe location data to generate a confidence score.

20. The system of claim 1 wherein the impedance characteristic comprises a change in a magnitude of tunneling current impedance at a predetermined frequency.

* * * * *